United States Patent
Alexander et al.

(10) Patent No.: US 9,993,206 B2
(45) Date of Patent: Jun. 12, 2018

(54) SYSTEM FOR CHARACTERIZING BRAIN CONDITION

(71) Applicant: Wisconsin Alumni Research Foundation, Madison, WI (US)

(72) Inventors: Andrew Lafayette Alexander, Madison, WI (US); Douglas Carl Dean, III, Fitchburg, WI (US); Gregory Russel Kirk, Madison, WI (US); Brittany Gail Travers, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days. days.

(21) Appl. No.: 15/342,391

(22) Filed: Nov. 3, 2016

(65) Prior Publication Data

US 2018/0116603 A1    May 3, 2018

(51) Int. Cl.
| | |
|---|---|
| *G06K 9/00* | (2006.01) |
| *A61B 5/00* | (2006.01) |
| *G06F 17/11* | (2006.01) |
| *G06T 7/00* | (2017.01) |
| *G06K 9/62* | (2006.01) |

(Continued)

(52) U.S. Cl.
CPC .......... *A61B 5/7275* (2013.01); *A61B 5/0042* (2013.01); *A61B 5/055* (2013.01); *A61B 5/4064* (2013.01); *G01R 33/4828* (2013.01); *G01R 33/5602* (2013.01); *G01R 33/56341* (2013.01); *G06F 17/11* (2013.01); *G06K 9/6202* (2013.01); *G06T 7/0012* (2013.01); *G06T 7/0081* (2013.01); *G06T 2207/10088* (2013.01); *G06T 2207/30016* (2013.01)

(58) Field of Classification Search
USPC ....... 382/100, 103, 106, 128–134, 154, 162, 382/168, 173, 181, 189, 199, 219, 232, 382/254, 274, 276, 286–294, 305, 312; 600/410, 407; 324/309; 378/21
See application file for complete search history.

(56) References Cited

U.S. PATENT DOCUMENTS 9,245,334 B2  1/2016  Lipton et al.
2008/0051649 A1*  2/2008  O'Dell .................. A61B 5/055
                                                      600/410

(Continued)

FOREIGN PATENT DOCUMENTS

WO        206011137 A1    1/2016

OTHER PUBLICATIONS

Namhee Kim et al.; "Whole brain approaches for identification of microstructural abnormalities in individual patients: comparison of techniques applied to mild traumatic brain injury." PloS one 8, No. 3 (Mar. 2013): e59382. pp. 1-14; US.

(Continued)

*Primary Examiner* — Seyed Azarian
(74) *Attorney, Agent, or Firm* — Boyle Fredrickson, S.C.

(57) ABSTRACT

A sensitive measure of brain condition simultaneously evaluates multiple measurements of water diffusion in brain tissue combined so as to correct for covariance between the different data types of the multipoint measurements and compares the multipoint measurements to a corresponding multipoint measure representing normal brain tissue to provide a distance indicating a likelihood of atypical brain conditions.

10 Claims, 3 Drawing Sheets

(51) Int. Cl.
*A61B 5/055* (2006.01)
*G01R 33/563* (2006.01)
*G01R 33/56* (2006.01)
*G01R 33/48* (2006.01)
*A61B 5/05* (2006.01)

(56) References Cited

U.S. PATENT DOCUMENTS

2009/0270712 A1* 10/2009 Raghavan ............ A61M 5/1723
  600/407
2010/0004527 A1* 1/2010 Dale ................ G01R 33/56341
  600/410
2011/0199084 A1* 8/2011 Hasan .................... A61B 5/055
  324/309
2013/0223714 A1* 8/2013 Lipton .................. G06T 7/0012
  382/131

OTHER PUBLICATIONS

Michael L. Lipton et al.; "Robust detection of traumatic axonal injury in individual mild traumatic brain injury patients: intersubject variation, change over time and bidirectional changes in anisotropy." Brain imaging and behavior 6, No. 2 (Jun. 2012); pp. 329-342; US.

* cited by examiner

SYSTEM FOR CHARACTERIZING BRAIN CONDITION

STATEMENT REGARDING FEDERALLY SPONSORED RESEARCH OR DEVELOPMENT

This invention was made with government support under MH097464 and NS092870 awarded by the National Institutes of Health. The government has certain rights in the invention.

CROSS REFERENCE TO RELATED APPLICATION

--

BACKGROUND OF THE INVENTION

The present invention relates to a diagnostic apparatus and method for evaluating brain condition, and in particular, to a method combining quantitative data from a magnetic resonance imaging (MRI) system for improved characterization of brain condition and in particular brain trauma or injury.

Brain injury and in particular mild traumatic brain injury (mTBI) can be structurally subtle and thus largely invisible to standard qualitative imaging techniques. For this reason, standard and widely used diagnostic tools such as CT and MRI imaging are largely unsuccessful in characterizing brain abnormalities associated with such injury.

Quantitative MRI imaging, such as diffusion-weighted imaging (DWI), holds more promise in characterizing brain trauma. The measurement of water diffusion in brain tissue can indicate, for example, swelling (edema) or scarring in the brain tissue associated with trauma. Changes in anisotropy of diffusion of water in brain tissue can also reveal changes in the organizational structure of the brain, for example, caused by axonal injury (e.g., shearing). Such injury can disrupt the path of water diffusion associated with white matter neural tracts. Such neural tracts can be visualized by Diffusion Tensor Imaging (DTI), for example. Fractional Anisotropy (FA) derived from DTI has been used to assess changes in brain microstructure associated with axonal injury.

Different types of brain injury are highly variable in terms of severity, brain location, and type of pathology (e.g., axonal shearing, hemorrhage, edema, glial death, etc.) making it difficult to accurately assess brain trauma using these quantitative measures. For example, brain trauma can cause either increased fractional anisotropy or decreased fractional anisotropy in different cases. Variations in patient history and characteristics such as age can make it challenging to assess brain trauma from the quantitative information provided by techniques such as fractional anisotropy.

SUMMARY OF THE INVENTION

The present invention provides a more robust and sensitive measure of brain trauma by combining different quantitative brain imaging measurements. This combination corrects for covariance between the different measures in a way that emphasizes the unique qualities of the different measures that otherwise might be overwhelmed by their similarities. The combined measures may be compared to a similar combination for patients without brain trauma allowing a comprehensive detection of deviations from those normal values (for example, either increased or decreased diffusion anisotropy) better capturing the effects of a broad range of different types of trauma.

Specifically, in one embodiment, the invention provides a system for assessing brain condition employing a magnetic resonance imaging system producing at least two different quantitative image data sets based on different imaging protocols or processing systems. The quantitative image sets provide data values at different locations within the brain. The processing system combines the data values at a given location corrected by the correlation among the types of data of the different data values and then compares the corrected data values of the given location to corresponding data values representing a normal brain to measure a difference revealing brain condition.

It is thus a feature of at least one embodiment of the invention to combine different related measurements in a way that reveals the differences between the measurements as opposed to simply emphasizing their common features. By correcting the different measures for their covariance (that is, how they naturally vary with each other), the different sensitivities of these measures can be exploited for distinguishing brain conditions.

The different quantitative image data sets may each provide measures of diffusion of water in the brain.

It is thus a feature of at least one embodiment of the invention to obtain additional data dimensions from diffusion measurements, for example, which can be extracted from a single acquisition data set.

The diffusion measures may include mean diffusion and fractional anisotropy.

It is thus a feature of at least one embodiment of the invention to separately analyze different qualities of diffusion with respect to its amount (revealed by mean diffusion) and anisotropy (revealed by fractional anisotropy).

The different quantitative image data sets may further include non-diffusion weighted imaging methods including susceptibility or T2*-weighted imaging, T1 or T2 relaxometry, multicomponent relaxometry, magnetization transfer imaging, chemical shift or spectroscopic data, blood flow imaging, or exogenous contrast agent enhancement.

It is thus a feature of at least one embodiment of the invention to provide yet another dimension of data that can be obtained from a single MRI acquisition.

The combination of different measures may create a multidimensional vector and the comparison may compare the multidimensional vector so created against a multidimensional vector representing a normal value of the brain.

It is thus a feature of at least one embodiment of the invention to provide a multidimensional comparison of an individual patient to a normal multidimensional value representing patients without brain trauma or other atypical conditions.

The multidimensional vector indicating a normal value of the brain may be a weighted composite of multiple normal individuals.

It is thus a feature of at least one embodiment of the invention to provide a normal relevant to a wide variety of different individuals.

The system may apply at least one threshold to the difference to develop two or more quantitative brain condition categories.

It is thus a feature of at least one embodiment of the invention to provide an intuitive categorization of brain conditions useful for physicians to assess brain trauma.

The different image sets may provide measures for multiple different volume locations in the brain.

It is thus a feature of at least one embodiment of the invention to permit more sensitive independent assessment of specific brain regions without averaging effects over the entire brain.

The system may further match volume locations between the two different imaging sets to corresponding volume locations of the normal data to evaluate differences between corresponding volume locations.

It is thus a feature of at least one embodiment of the invention to provide a registration between brain regions of the patient and normal data permitting region-to-region direct comparisons such as may improve the discrimination of the technique as opposed to comparisons of broad spatially in different metrics.

The system may output an image representing the brain and may depict the differences between these measures and normal at the locations of the corresponding volume locations.

It is thus a feature of at least one embodiment of the invention to provide an additional diagnostic dimension to standard qualitative MRI imaging.

The combination and correction for covariance may employ the Mahalanobis distance.

It is thus a feature of at least one embodiment of the invention to provide a simple and robust distance-based statistical tool for combining multiple measurements that have high correlations.

These particular objects and advantages may apply to only some embodiments falling within the claims and thus do not define the scope of the invention.

DETAILED DESCRIPTION OF THE PREFERRED EMBODIMENT

Figure 1:
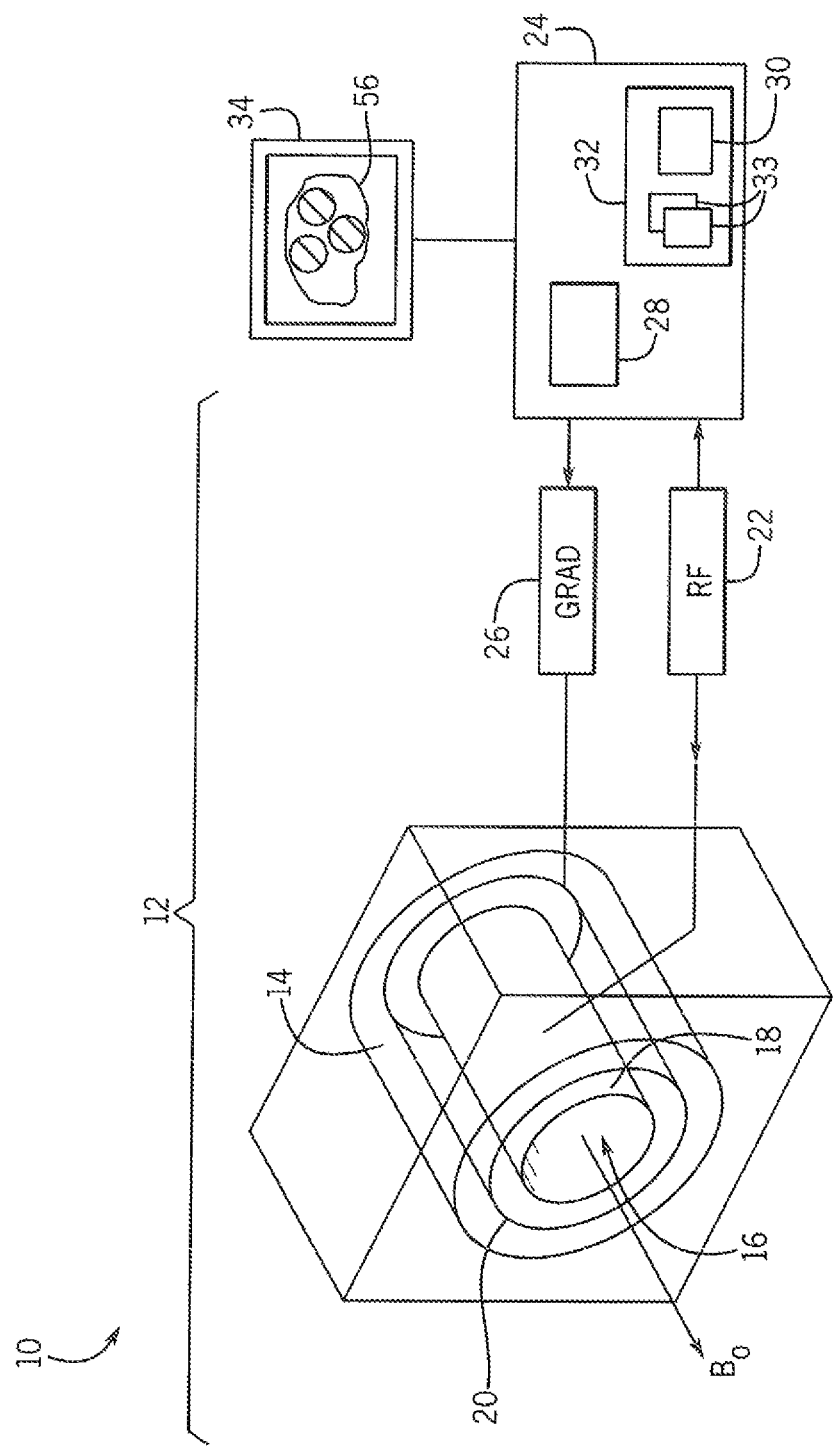
FIG. 1 is a simplified diagram of a system for implementing the present invention including a magnetic resonance imaging apparatus and associated computer processor executing a stored program and communicating with an image display.

Referring now to FIG. 1, a system 10 for assessment of brain trauma may include a magnetic resonance machine 12 for acquiring images of a brain of a patient (not shown). As generally understood in the art, such systems 10 may include a polarizing (typically superconducting) magnet 14 establishing a polarizing magnetic field Bo within a magnet bore 16 sized to receive a patient therein.

One or more radiofrequency coils 18 positioned about the bore may apply a radiofrequency stimulation signal to the patient inducing precession in magnetically polarized water nuclei of the patient's brain. The phase and frequency of these precessing nuclei may be adjusted by magnetic gradient fields applied in multiple dimensions applied through different gradient coils 20 to encode position information into these nuclear precessions. Faint radiofrequency signals from the precessing nuclei are then received by the radiofrequency coils 18 and passed to a radiofrequency processing circuit 22 for extraction of a magnetic resonance imaging signal.

A system computer 24 associated with the magnetic resonance machine 12 may control the radiofrequency processing circuit 22 to produce the desired radiofrequency stimulation pulses and to receive the magnetic resonance imaging signal of the processing signal at various gradient field encodings for processing. In this regard, the system computer 24 may control gradient amplifiers 26 for applying the necessary magnetic gradients to the patient during the imaging process in implementing an imaging sequence of various types known in the art. The system computer 24 may include one or more processors 28 executing a stored program 30 held in a memory 32 for implementing the image sequences and for reconstructing the magnetic resonance imaging signals into qualitative and quantitative images 33, for example, that may be stored and or displayed on an associated display 34.

An example MRI system suitable for use with the present invention is a three Tesla MRI machine available from Siemens under the tradename of Magnetom Trio capable of implementing diffusion-weighted and susceptibility-weighted imaging on a human patient.

Figure 2:
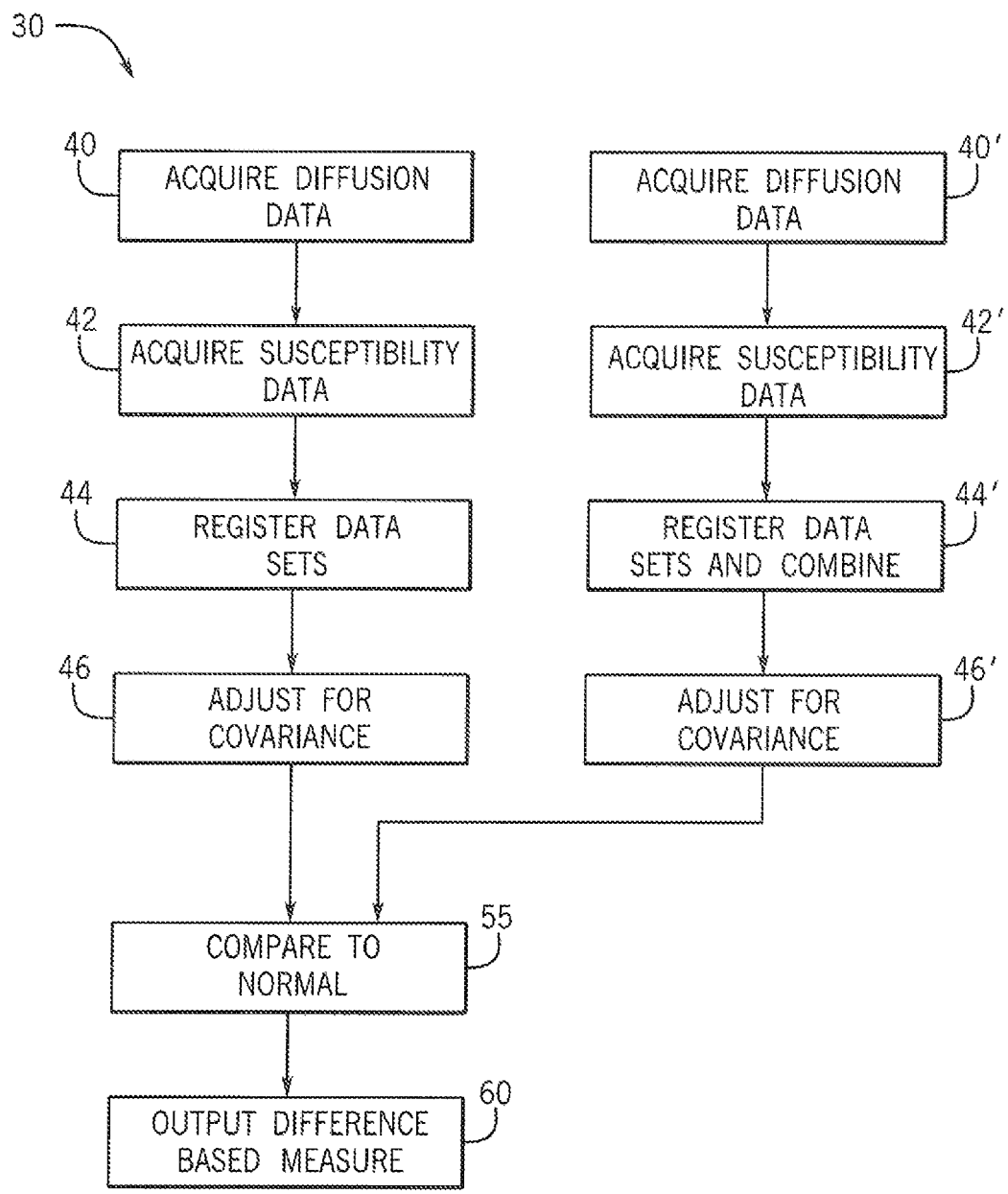
FIG. 2 is a flowchart showing the steps of the program of the computer processor of FIG. 1.

Referring now also to FIG. 2, the MRI machine 12, as operated according to the stored program 30 executed by the system computer 24, may acquire diffusion data of a patient with possible traumatic brain injury (minor or otherwise) as indicated by process block 40 using standard diffusion-weighted imaging protocols which provide quantitative diffusion tensors for a range of voxels within the patient's brain. In this process, multiple quantitative images are co-registered and corrected for distortion, translation, rotation, and eddy currents, for example, using an affine registration tool using manual or automatic fiducial point locating. The multiple quantitative images may then be used to produce diffusion tensors for each image voxel using, for example, an outlier rejection algorithm such as the RESTORE algorithm described in Chang L C, Jones D K, Pierpaoli C. RESTORE: Robust estimation of tensors by outlier rejection. Magn Reson Med 2005; 53: 1088-1095.

As will be appreciated to those of ordinary skill in the art, the diffusion tensors provide a direction and magnitude of diffusion for each voxel and can then be analyzed to provide any of the measures of fractional anisotropy (FA), mean diffusivity (MD), axial diffusivity (AD) and radial diffusivity (RD) measures. These different measures will be termed "types" of data. Generally fractional anisotropy provides a scalar value for each voxel indicating the degree of anisotropy associated with each voxel's diffusion. Diffusion that is identical in all directions would have an anisotropy of zero whereas diffusion along a single direction would have an anisotropy of one. FA is sensitive to micro-structural changes in the brain but less specific with respect to the type of change.

Mean diffusivity provides a scalar value for each voxel indicating the magnitude of the diffusivity of the voxel average in all directions. Mean diffusivity is sensitive to edema and necrosis such as affect diffusivity generally and roughly provides an inverse measure of membrane density.

Radial diffusivity is a scalar value indicating the amount of water diffusion perpendicular to the white matter fibers. Radial diffusivity increases in white matter with de-myelination.

Axial diffusivity is a scalar value indicating the amount of water diffusion parallel to the white matter fibers. Axial diffusivity decreases in white matter after significant chronic injury.

At succeeding process block 42, additional image data may be obtained, for example, susceptibility data also termed $T_2^*$ image data. Generally, susceptibility weighted imaging may also be used as a basis for diffusion-weighted imaging; however, the acquisition at process block 42 is of a type providing scalar values indicating susceptibility for each voxel as opposed to diffusion for each voxel. Alternatively, the susceptibility data may be obtained simultaneously during the acquisition of the diffusion data of process block 40 when that diffusion data is extracted using susceptibility weighting.

Referring now to process block 44, the data collected in process blocks 40 and 42 may be registered to a standard registration template for the human brain, for example, using an affine registration tool and manual or automatic fiducial location in the same manner as used to register the multiple diffusion-weighted images of process block 40, but in this case to the standard registration template rather than to the patient him or herself.

The registered data can also be divided into standard segments associated with the registration template, for example, each segment representing a different anatomical brain region including standard anatomical divisions, white matter tracts, or the like. Alternatively, the single segment of the whole brain may be used. Also at this time, other confounding effects, such as patient age or other types of individual variability (e.g., gender, IQ, or the like) may be regressed out of the registered data using standard statistical techniques.

Figure 3:
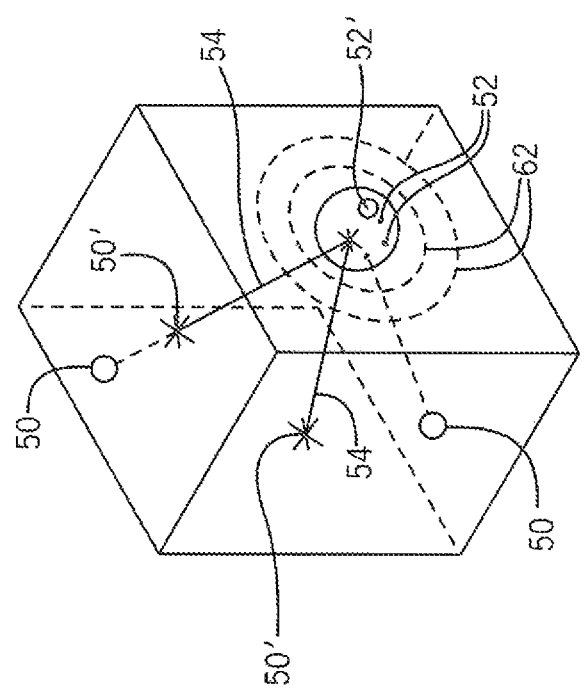
FIG. 3 is a simplified pictorial representation of the comparison process of multidimensional values used in the present invention.

Referring now to FIGS. 2 and 3, at process block 46, multiple of the measures processed in process blocks 40, 42, and 44 for each voxel may be combined (for example, averaged) within a data type for each segment to produce multidimensional vector 50 for each anatomical brain region. Each vector element averages the data of a given data type within the segment and may be visualized, for example, as a point in N-space where N is the number of different types of data. For example, in the case of using FA, MD, and $T_2^*$ data, each multidimensional vector 50 will have three dimensions for each segment. The invention contemplates additional dimensions may also be used.

This vector 50 is then corrected to account for the covariance between these different data types of the vector which otherwise would dominate the measure provided by the combined vector 50. Specifically to the extent that the data types tend to move in value together (for example, based on the same underlying feature of the brain) this common movement is de-weighted to emphasize the independent movements of the data type. This de-weighting can be done by establishing a correlation or covariance between each of these different types of data, for example, empirically, and using that established covariance to adjust the measures appropriately. The result is a corrected vector 50'.

Referring again to FIG. 2, the process of process blocks 40, and 42 may also be performed again for multiple patients as indicated by process blocks 40' and 42' to provide multiple, multipoint vectors 52 for individuals who do not have brain injury. These multipoint vectors 52 may be averaged (on a data type basis and as registered per process block 44') to establish a normal multipoint vector 52' in N-space that may be corrected for correlation between the data types per process block 46' to provide a corrected multipoint vector 53 used to identify a degree of brain trauma.

Specifically, per process block 55, the vectors 50' for each segment and the multipoint vector 53 may be compared by establishing a Euclidean distance 54 between each vector 50' associated with a particular segment and the corrected multipoint vector 53 such that a greater distance indicates an increased likelihood of brain trauma for that particular anatomical region. This distance 54 thereby represents a comparison or difference between the given patient being assessed for brain trauma and a normal brain as represented by multipoint vector 53. Note that deviations from the multipoint vector 53 in multiple directions can thereby be accommodated so that the present invention can capture, for example, abnormal increases and decreases in the diffusion measures.

Figure 4:
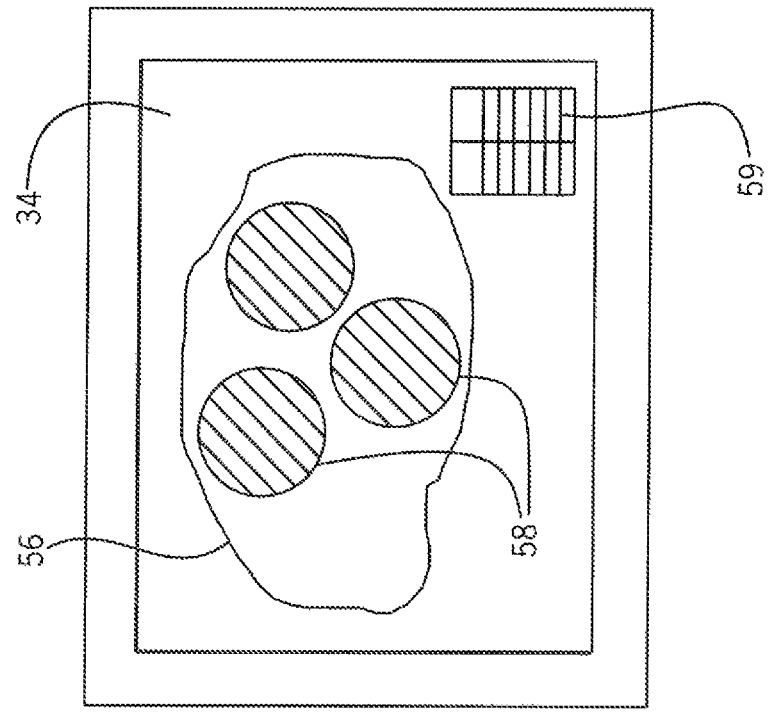
FIG. 4 is a depiction of the image display of FIG. 1 in one embodiment superimposing brain trauma information over a standard qualitative MRI image.

Referring to process block 60 and also to FIG. 4, this likelihood for each particular anatomical region may be displayed quantitatively in a table 59 or, for example, on a display 34 showing a standard MRI image of the brain 56 with each anatomical segment 58 shaded or colored to show the value of the distances 54 for that tissue of that segment. This image may be three-dimensional and rotatable to permit identification of the locations of the possible trauma and to view other features of the brain revealed by the standard imaging.

Referring to both FIGS. 3 and 5, the measured distance 54 associated with each segment 58 may be applied against a threshold distance 62 or multiple such thresholds to categorize that distance 54 into distinct categories of degree of trauma, for example, with a color red indicating a high likelihood of trauma above a predetermined first threshold 62 and green indicating a low likelihood of trauma below the first threshold 62. The threshold distance 62, for example, may be based on a Gaussian distribution of the data of the individuals without brain trauma, for example, being at a first standard deviation of that distribution.

The process of adjusting for covariance of process block 46 and 46' and comparing the adjusted vectors 50' and 53 of process block 55 may be performed in a single step by evaluating a Mahalanobis distance between the vector 50' and 53 of a type described, for example, in Mahalanobis P C, On the Generalized Distance in Statistics, Proceedings of the National Institute of Sciences (Calcutta) 1936; 2: 49-55, and using the equation:

$$D_M = \sqrt{(\vec{x} - \mu)S^{-1}(\vec{x} - \mu)^T}$$

where $\vec{x}$ corresponds to the set of multivariate observations of vector 50', $\mu$ is the mean of the multivariate observations of vector 52', and S corresponds to the covariance matrix of the multivariate measures. In this way, $D_M$ provides the distance 54 and accounts for the variance of individual observations as well as the covariance between the set of observations.

The invention contemplates that additional data sets, including both imaging and non-imaging types of data, may be combined with the diffusion and susceptibility measurements described above. For example, this additional data may include other types of quantitative imaging (e.g., PET), proteins or chemical markers, cognitive/behavioral testing measures (e.g., IMPACT, reaction speed), electrophysiological measures (EEG, MEG, EMG), or fluid markers (serum, CSF) and the like.

It will be appreciated that the present technique may also be used to perform longitudinal studies on groups or individuals by comparing current measures of the individuals as vector 50' to earlier measures of the individuals as vector 53 so as to accurately detect changes in the brain associated with recovery or the like.

Example I

A pilot study of this technique was conducted using forty-four patients with mild traumatic brain injury and sixteen control patients without traumatic brain injury. The acquired MRI data of each of these patients was used to determine fractional anisotropy, mean diffusivity, axial diffusivity, and radial diffusivity for a variety of standard anatomical brain segments. Notably, fractional anisotropy values both increased and decreased in particular anatomical segments for patients with traumatic brain injury and either increased or decreased in only twenty-five out of forty-four cases. Similarly mean diffusion both increased and decreased in patients with traumatic brain injury, either increasing or decreasing in only fifteen out of the forty-four traumatic brain injury cases.

All forty-four traumatic brain injury patients were identifiable as having a Mahalanobis distance 54 of greater than two with respect to the normal and thirty out of the forty-four traumatic brain injury patients had a Mahalanobis distance of greater than 3. It will be understood that the processor 28 used for the invention may be associated with the MRI machine 12 or may be an off-line processor receiving data from a processor associated with the MRI system. As used herein, the term processor should be held to embrace both a single processor and multiple processors communicating with each other Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

As noted above, references to "a computer" and "a processor" can be understood to include one or more systems that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A system for assessing brain condition comprising:
a magnetic resonance imaging system providing at least two quantitative image data sets generated by the magnetic resonance imaging system and providing different types of data each based on different imaging protocols, each quantitative image data set providing data values at different locations within a brain; and
a processor executing a stored program to receive the at least two different quantitative image data sets from the magnetic resonance imaging system and:
(a) combining data values of different types of data of the at least two quantitative image data sets at given locations corrected by correlation among the different types of data of the data values; and
(b) comparing the corrected data values of the given locations to corresponding data values representing a normal brain to provide a difference revealing a brain condition;
wherein the combining creates a multidimensional vector and the comparing determines a value related to a Euclidean distance between a point represented by the multidimensional vector and a point represented by a multidimensional vector of the corresponding data values representing a normal brain.

2. The system of claim 1 wherein the at least two different quantitative image data sets provide measures of diffusion of water in the brain.

3. The system of claim 2 wherein the at least two different quantitative image data sets include mean diffusion and fractional anisotropy.

4. The system of claim 3 wherein the at least two different quantitative image data sets include including susceptibility or T2*-weighted imaging without diffusion measurement.

5. The system of claim 1 wherein the multidimensional vector of the corresponding data values representing a normal brain is a weighted composite of multiple normal individuals.

6. The system of claim 1 further applying at least one threshold to the difference to develop two or more quantitative brain condition categories.

7. The system of claim 1 wherein the data values at different locations within the brain are combined according to predetermined brain segments and wherein the comparing compares combined data values of a given brain segment with corresponding combined data values representing a normal brain for a segment corresponding to the given brain segment.

8. The system of claim 1 wherein step (b) further matches volume locations between the at least two different quantitative image data sets to corresponding volume locations of the normal data to evaluate differences between corresponding volume locations.

9. The system of claim 8 further outputting an image representing the brain and depicting the differences at the volume locations of corresponding volume locations.

10. The system of claim 1 wherein the steps of (a) and (b) use Mahalanobis distance.

* * * * *